US007615187B2

(12) United States Patent  
Helton et al.

(10) Patent No.: US 7,615,187 B2  
(45) Date of Patent: Nov. 10, 2009

(54) ORGANIC PEROXYACID PRECURSORS

(75) Inventors: Danny O. Helton, Newbury, FL (US); David W. Hobson, Boerne, TX (US)

(73) Assignee: D H Technologies, LLP, Boerne, TX (US)

( * ) Notice: Subject to any disclaimer, the term of this patent is extended or adjusted under 35 U.S.C. 154(b) by 307 days.

(21) Appl. No.: 11/895,384

(22) Filed: Aug. 24, 2007

(65) Prior Publication Data

US 2007/0297941 A1   Dec. 27, 2007

Related U.S. Application Data

(63) Continuation-in-part of application No. 10/800,788, filed on Mar. 16, 2004, now Pat. No. 7,307,191, which is a continuation-in-part of application No. 10/752,430, filed on Jan. 6, 2004, now Pat. No. 7,005,549.

(60) Provisional application No. 60/438,114, filed on Jan. 6, 2003.

(51) Int. Cl.  
A61L 2/00     (2006.01)  
C11D 7/32    (2006.01)  
C11D 7/34    (2006.01)  
C11D 7/38    (2006.01)  
C11D 7/54    (2006.01)

(52) U.S. Cl. .................. 422/28; 564/154; 564/192; 568/31; 252/186.38; 510/376; 510/492; 510/499; 510/505; 510/501

(58) Field of Classification Search .............. 422/28; 564/154, 192; 568/31; 252/186.38; 510/376, 510/492, 499, 501, 505  
See application file for complete search history.

(56) References Cited

U.S. PATENT DOCUMENTS

| | | | |
|---|---|---|---|
| 3,267,139 A | 8/1966 | Lafferty | 564/79 |
| 3,956,396 A | 5/1976 | Mageli et al. | 260/610 |
| 4,151,106 A | 4/1979 | Meenen | 252/186 |
| 4,255,277 A | 3/1981 | Smearing | 252/186 |
| 4,396,527 A | 8/1983 | Matsuyama et al. | 252/186.23 |
| 4,401,663 A | 8/1983 | Buckwalter et al. | 424/321 |
| 4,842,765 A | 6/1989 | Satomi | 252/186.26 |
| 4,917,816 A | 4/1990 | Self | 252/186.26 |
| 5,057,479 A | 10/1991 | Bock | 502/160 |
| 5,110,495 A | 5/1992 | Self | 252/186.26 |
| 5,162,280 A | 11/1992 | Bock | 502/160 |
| 5,596,017 A | 1/1997 | Otsu et al. | 514/517 |
| 5,654,464 A | 8/1997 | Abma et al. | 558/261 |
| 5,773,459 A | 6/1998 | Tang et al. | 514/445 |
| 6,174,922 B1 | 1/2001 | Arnold et al. | 514/604 |
| 6,303,816 B1 | 10/2001 | Arnold et al. | 564/82 |
| 6,500,865 B1 | 12/2002 | Zarrinmayeh et al. | 514/605 |

FOREIGN PATENT DOCUMENTS

| | | |
|---|---|---|
| DE | 1801713 | 6/1970 |
| DE | 1953920 | 5/1971 |

*Primary Examiner*—Gregory R Del Cotto  
(74) *Attorney, Agent, or Firm*—Christopher Whewell

(57) ABSTRACT

This present invention provides materials for use as solid or concentrated chemical precursors for the production of organic peroxy acids (peracids). Organic peroxy acids are formed using a precursor according to the invention when they are combined with hydrogen peroxide or a hydrogen peroxide precursor such as a percarbonate or a perborate in aqueous medium. Organic peroxy acids, such as peroxyacetic acid, are used currently to disinfect medical equipment such as endoscopes and related items.

31 Claims, No Drawings

ORGANIC PEROXYACID PRECURSORS

CROSS-REFERENCE TO RELATED APPLICATIONS

This application is a Continuation-In-Part of U.S. patent application Ser. No. 10/800,788 filed Mar. 16, 2004, now U.S. Pat. No. 7,307,191, which was itself a Continuation-In-Part of U.S. patent application Ser. No. 10/752,430 filed on Jan. 6, 2004, now U.S. Pat. No. 7,005,549, and claims the benefit of U.S. Provisional Application No. 60/438,114 filed Jan. 6, 2003 the entire contents of which are herein incorporated by reference.

TECHNICAL FIELD

This invention relates generally to processes for producing organic peroxy acids and more particularly to the use of chemical precursors from which peroxygen acids (peroxy acetic, peroxy propionic, etc.) may be advantageously prepared upon mixing the precursors with hydrogen peroxide or a source of peroxide, such as percarbonate or perborate anions.

BACKGROUND

Peroxy acids, and peroxyacetic acid in particular, have been used for cleaning and disinfecting various surfaces and implements, including medical devices such as endoscopes, and environmental surfaces, including countertops, ductwork, etc. However, one drawback associated with the use of solutions of peroxyacetic acid and other peroxy acids in general is that the shelf life of such solutions is limited to a few months, due to the inherent instability of the materials. Even very low concentrations of the peroxyacetic species, such as those used to disinfect surfaces (i.e., 0.05% to about 5%) are too unstable for a useful commercial shelf life.

One way to overcome shelf life issues may be to employ a solid formulation which is mixed with water shortly before needed. Active precursor components, including a solid form of hydrogen peroxide such as an alkali metal or alkaline earth metal percarbonate or perborate salt can be combined with an acyl donor, such as either tetraacetylethylenediamine ("TAED") or acetylsalicylic acid ("ASA") to yield a peroxy acid according to the scheme conducted in aqueous media:

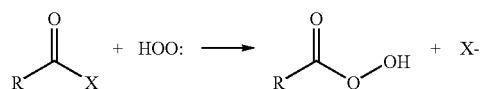

the peroxide being present from reaction of the perborate or percarbonate with water, which is subsequently available to react with the acyl compound. In the foregoing reaction, the radical X represents the remaining residue of the TAED or ASA molecule, such as in the case of ASA wherein it represents the ASA molecule minus the acetyl group. However, we do not consider TAED and ASA to be efficient acylating agents, in that a relatively large mass of useless carbon-containing byproducts are generated when these reactants are employed. In addition, the kinetics of the reaction are not as favorable as would be desired, because quick generation of appreciable quantities of peroxyacetic acid from ASA according to the above scheme requires a reaction temperature above room temperature.

While peroxyacetic acid has been used to disinfect medical equipment such as endoscopes and related items, peroxypropionic acid ("PPA") has not been developed for such purposes. Precursors according to one embodiment of the present invention have the distinct advantage that they can be used to easily produce novel antimicrobial formulations which contain PPA, as well as a whole host of other peroxy acids which consume less weight of hydrogen peroxide during their production per mole of peroxy acid produced, than commercial precursors acetyl salicylic acid (ASA) and tetraacetylethylenediamine (TAED). Additionally, precursors according to an embodiment of the present invention allow for the formulation of antimicrobial compositions that have room temperature stability in their concentrated forms, and which can alternatively be packaged in dry powder form for reconstitution by combination with hydrogen peroxide, or a hydrogen peroxide precursor/water mixture at the site of their end use. The resulting peroxide-containing liquids can be readily delivered in liquid or gaseous form at the site of use. The dry powder form of a compound according to one embodiment, or its concentrate may also be applied to the site of use and activated with hydrogen peroxide or water in combination with a hydrogen peroxide precursor.

Thus, in summary, provided are novel water-soluble precursors useful for efficiently generating peroxy acids. When using a precursor according to an embodiment of the present invention, there are less by-products generated for every mole of peroxy acid generated. Further, a smaller weight of the precursor provided by the present invention is required to generate a mole of peroxy acid than when using a prior art material and/or method. The acyl precursors provided by an embodiment of the present invention are generally more water-soluble than ASA, relatively inexpensive to manufacture, and consume less weight of acyl precursor per mole of peroxy acid generated than the corresponding ASA.

Uses for the solutions provided by the embodiments of the invention include, without limitation: emergency disinfection of wounds by mixing dry powder with water; disinfection of surgical facilities and medical treatment rooms; chemical sterilization of surgical equipment and instruments, particularly endoscopes; disinfection of medical devices; disinfection of animal enclosure areas such as used by horses, cattle, dogs, cats, etc.; remediation of mold in buildings, the contents of buildings; disinfecting plants and foodstuffs, including meats, vegetables, and fruits; disinfection of surfaces from vegetative bacteria, molds, fungi and their spores, especially for remediation in non-line-of-slight applications; and liquid disinfectants of equipment such as tanks, passenger cars, all military vehicles, aircraft, and related equipment.

SUMMARY OF THE INVENTION

Provided are compositions useful for forming peroxygen acids, which compositions comprise a nitrogenous compound having the structure:

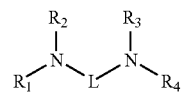

in which L is a divalent radical that is independently selected from the group consisting of:

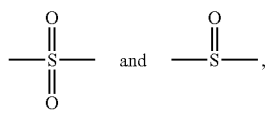

and wherein $R_1$, $R_2$, $R_3$, and $R_4$ are each independently selected from the group consisting of: hydrogen, any $C_1$ to $C_{20}$ hydrocarbyl group, and the group:

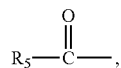

subject to the proviso that: at least one of $R_1$, $R_2$, $R_3$, and $R_4$ are the group:

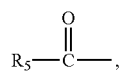

in which $R_5$ is in each occurrence independently hydrogen or any $C_1$ to $C_{20}$ hydrocarbyl group.

According to an alternate embodiment, one and only one of $R_1$, $R_2$, $R_3$, and $R_4$ is the group:

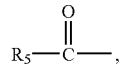

in which $R_5$ is independently hydrogen or any $C_1$ to $C_{20}$ hydrocarbyl group. A variant of such alternate embodiment is where at least one of the groups of $R_1$, $R_2$, $R_3$, and $R_4$ which are not the group:

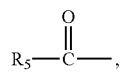

is hydrogen. Another variant is where at least one of the groups of $R_1$, $R_2$, $R_3$, and $R_4$ which are not the group:

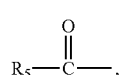

is independently in each occurrence any $C_1$ to $C_{20}$ hydrocarbyl group.

According to another alternate embodiment, any two of $R_1$, $R_2$, $R_3$, and $R_4$ are the group:

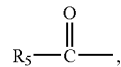

in which $R_5$ is independently in each occurrence hydrogen or any $C_1$ to $C_{20}$ hydrocarbyl group. One variant of this alternate embodiment is where at least one of the groups of $R_1$, $R_2$, $R_3$, and $R_4$ which are not a group:

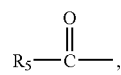

is hydrogen. Another variant of this alternate embodiment is where at least one of the groups of $R_1$, $R_2$, $R_3$, and $R_4$ which are not a group:

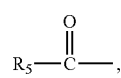

is independently in each occurrence any $C_1$ to $C_{20}$ hydrocarbyl group.

According to another alternate embodiment, any three of $R_1$, $R_2$, $R_3$, and $R_4$ are the group:

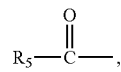

in which $R_5$ is independently in each occurrence hydrogen or any $C_1$ to $C_{20}$ hydrocarbyl group, and the group of $R_1$, $R_2$, $R_3$, and $R_4$ which is not a group:

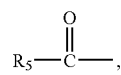

is hydrogen. One variant of this alternate embodiment is where the group of $R_1$, $R_2$, $R_3$, and $R_4$ which is not a group:

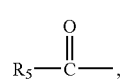

is any $C_1$ to $C_{20}$ hydrocarbyl group. Another variant of this alternate embodiment is where all of $R_1$, $R_2$, $R_3$, and $R_4$ are the group:

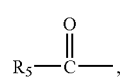

in which $R_5$ is independently in each occurrence hydrogen or any $C_1$ to $C_{20}$ hydrocarbyl group.

A fourth alternate embodiment is where $R_1$ and $R_4$ are represented by the group:

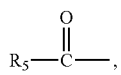

in which $R_5$ is independently in each occurrence hydrogen or any $C_1$ to $C_{20}$ hydrocarbyl group, and wherein $R_2$ and $R_3$ are each independently selected from the group consisting of: hydrogen, and any $C_1$ to $C_{20}$ hydrocarbyl group. A variant of this fourth general embodiment is where $R_5$ in each occurrence is selected from the group consisting of: methyl, ethyl, 1-propyl, and 2-propyl.

The aforesaid nitrogenous compounds are generally solids at room temperature, and it is a routine matter to dry them to powder form. Thus, is a simple matter to mix a nitrogenous compound of the invention with any number of other solid compounds which upon being contacted with water yield a peroxide, such as hydrogen peroxide and peroxide ions. Examples of such materials include alkali metal and alkaline earth metal salts of percarbonates and perborates. According to one embodiment, a composition is provided which comprises a dry powder that includes a nitrogenous compound according to one embodiment of the invention and a source of peroxide, and it is preferred that the nitrogenous compound is present between about 0.1% and about 5% by weight based on the total weight of said composition.

Also provided is a process for providing an aqueous peroxy acid comprising contacting a composition containing a nitrogenous compound according to an embodiment of the invention with an aqueous peroxide, such as hydrogen peroxide or any other source of peroxide ions. An aqueous solution provided according to one embodiment of the invention may contain water present in any amount between about 80% and about 99.95% by weight based on the total weight of the aqueous solution, and the nitrogenous compound(s) may be present in any amount between about 0.1% and about 10% by weight based upon the total weight of such aqueous solution, including any and all ranges therebetween. Various additives may be optionally included in such aqueous solutions, including buffers, surfactants, sequesterants, as such are known to those skilled in the art.

The invention also provides compositions which comprise an aqueous solution of a nitrogenous compound as set forth herein which further comprise at least one solid peroxide-generating compound which upon being contacted with water yields a peroxide, such as hydrogen peroxide or peroxide ions. Typical examples of suitable solid compounds include alkali metal and alkaline earth metal salts of percarbonates and perborates. One embodiment provides for the peroxide-generating compound to be present in any amount between about 0.01% and about 5% by weight based upon the total weight of the aqueous solution.

Also provided are methods for disinfecting surfaces by contacting any surface with a mixture comprising: water, any of the various nitrogenous compound provided herein, and any source of peroxide, such as hydrogen peroxide or peroxide ions.

Also provided are methods for volatilizing a peroxy acid by mixing water, a nitrogenous compound described herein, and a source of peroxide, such as hydrogen peroxide or peroxide ions, under conditions sufficient to enable evolution of a peroxy acid vapor from aqueous solution, or liberation of a peroxy acid vapor from an aqueous solution. Many peroxy acids are sufficiently volatile so as to auto-vaporize at room temperature and pressure. However, one alternate form of the invention employs conventional vaporization equipment and methods such as sonication, heating, and venturi effect to provide vapors of peroxy acids. Such known equipment and methods can be used with peroxy acids that are readily volatilized, and for providing vapors of peroxy acids that don't readily volatilize on their own.

DETAILED DESCRIPTION

One embodiment of the present invention provides chemical precursors from which organic peroxy acids may be prepared upon their being mixed with hydrogen peroxide or other peroxide precursors, such as percarbonates or perborates anions or species, in aqueous media. The nitrogenous compounds useful in accordance with the invention include those described by the chemical formula:

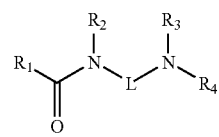

in which L is a divalent radical that is independently selected from the group consisting of:

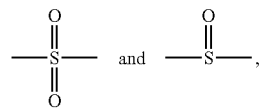

and wherein $R_1$ is independently any $C_1$ to $C_{20}$ hydrocarbyl group; $R_2$ is independently selected from the group consisting of: hydrogen, any $C_1$ to $C_{20}$ hydrocarbyl group, and the group:

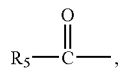

in which $R_5$ is independently hydrogen or any $C_1$ to $C_{20}$ hydrocarbyl group; $R_3$ is independently selected from the group consisting of: hydrogen and any $C_1$ to $C_{20}$ hydrocarbyl group; and $R_4$ is independently selected from the group consisting of: hydrogen, and the group

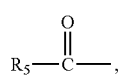

in which $R_5$ is independently hydrogen or any $C_1$ to $C_{20}$ hydrocarbyl group.

The nitrogenous compounds of this embodiment can be conveniently prepared by reacting an acid halide of a carboxylic acid with various substituted or unsubstituted sulfamides and sulfoxamides in an appropriate solvent, as known to those skilled in the art. An acid halide of a carboxylic acid is often referred to by those skilled in the art as simply an "acid halide". Acid halides of carboxylic acids, (including without limitation alkyl carboxylic acids, aryl carboxylic acids and alkylaryl carboxylic acids), are well known in the art, and are believed to be described in all reputable college-level organic chemistry textbooks, one example being "Introduction to Organic Chemistry", by Streitweiser and Heathcock, $2^{nd}$ ed. MacMillan Publishing Company, New York (1981), the entire contents of which are herein incorporated by reference, especially pages 517, et seq. The acid halides of carboxylic acids may be formed as the reaction product between a carboxylic acid and a suitable halogenating agent such as the trichloride and pentabromide of phosphorous, or the thionyl halides such as thionyl chloride and thionyl bromide, under conditions well known to the organic chemist. In the formation of acid halides by this route, the hydroxy group of the carboxylic acid function is replaced by a halogen atom, usually chlorine or bromine. Thus, in general, an acid halide useful for forming a nitrogenous compound in accordance with the present invention has the chemical structure:

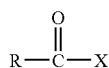

in which R is any $C_1$ to about $C_{20}$ hydrocarbyl group, and in which X is any halogen atom. This definition includes the acid halides of alkyl carboxylic acids, as well as the acid halides of aryl carboxylic acids and alkylaryl carboxylic acids. According to one preferred form of the invention, the halogen atom X comprises bromine or chlorine.

The term "hydrocarbyl", when referring to a substituent or group in the present specification and the claims appended hereto is used in its ordinary sense, which is well-known to those skilled in the art. Specifically, it means a group having a carbon atom directly attached to the remainder of the molecule and having predominantly hydrocarbon character. Examples of hydrocarbyl substituents or groups include: (1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical); (2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy); (3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group. All hydrocarbyl groups are useful within the meaning of R in the above formula for the acid halide, subject to the proviso that no portion of the hydrocarbyl radical R present is detrimentally reactive with the labile carbonyl-halogen bond also present within the time frame of the use of such acid halide in preparation of the targeted precursor.

Thus, typical acid halides suitable for use in preparing a precursor according to the present invention include, without limitation: acetyl chloride, adipoyl chloride, anisoyl chloride, acryloyl chloride, butyryl chloride, camphoroyl chloride, caproyl chloride, cinnamoyl chloride, cyanoacetyl chloride, formyl chloride, proprionyl chloride, fumaroyl chloride, glutaryl chloride, isophthaloyl chloride, levulinoyl chloride, lauroyl chloride, malonyl chloride, oleoyl chloride, oxalyl chloride, pyruvoyl chloride, salicyloyl chloride, stearoyl chloride, suberoyl chloride, terephthaloyl chloride, thioacetyl chloride, phthaloyl chloride, succinyl chloride, benzoyl chloride, maleyl chloride and toluoyl chloride. In fact, all known acid halides can be useful as acid halides from which a precursor according to the invention may be provided, owing to the presence of an active hydrogen atom in the molecular structure of the co-reactant with which the acid halide is reacted to form the inventive precursors.

The co-reactant used as a precursor with which an acid halide is reacted in order to form a nitrogenous compound provided by or useful in accordance with the invention is selected from the group consisting of substituted or unsubstituted sulfamides and sulfoxamides. Sulfamide is a compound well-known to have the structure:

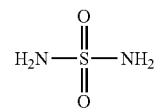

and sulfoxamide is a compound well known in the art to have the structure:

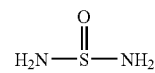

Each of these compounds comprise two nitrogen atoms, each of which have at least one active hydrogen atom attached thereto. For purposes of this invention and the appended claims, a hydrogen atom attached to a nitrogen atom of a substituted or unsubstituted sulfamide or sulfoxamide is considered to be an active hydrogen atom if it is capable of participating in the Zerevitinov reaction (Th. Zerevitinov, Ber. 40, 2023 (1907)) to liberate methane from methylmagnesium iodide. Further, each of these compounds sulfamide and sulfoxamide continue to contain an active hydrogen atom when one or more of their nitrogen atoms are mono-substituted with a hydrocarbyl group, thus rendering them reactive with an acid halide and suitable for use in providing a nitrogenous compound according to the invention. For convenience, the substituted and unsubstituted sulfamides and sulfoxamides that may be used as an initial raw material in providing a composition or compound that is useful according to embodiments the invention may be collectively denoted as:

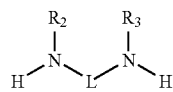

in which L is a divalent radical that is selected from the group consisting of:

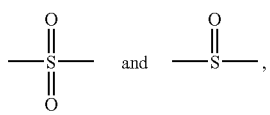

and wherein $R_2$ and $R_3$ are each independently selected from the group consisting of: hydrogen and any $C_1$ to $C_{20}$ hydrocarbyl group.

Thus, the preparation of a precursor according to one preferred embodiment of the invention may be accomplished by conducting the reaction:

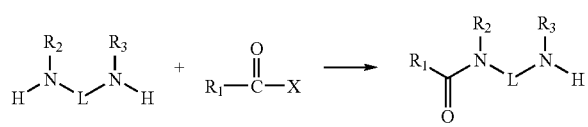

with the L and R groups being as herein defined. In such reaction, one mole of acid halide is shown to be reacted with each mole of substituted or unsubstituted sulfamide (or sulfoxamide when selected) reactant, and although not specifically written, in the process a mole of hydrogen halide HX is liberated. However, those of ordinary skill in the art readily appreciate that more than one mole of acid halide may be employed per mole of sulfamide (or sulfoxamide when selected). Particularly, when $R_2$ and $R_3$ are both hydrogen, it is possible to append up to four groups having structure:

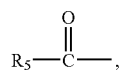

in which $R_5$ is independently hydrogen or any $C_1$ to $C_{20}$ hydrocarbyl group, to the starting material:

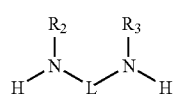

Thus, one embodiment of the invention provides a precursor which may be formed according to the reaction:

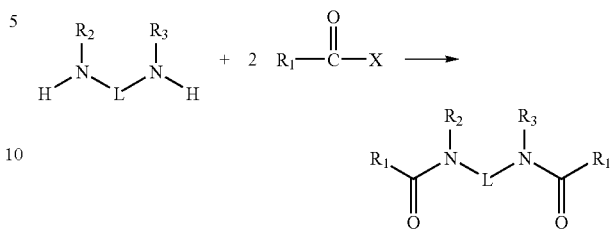

in which 2 moles of the same acid halide are reacted with each mole of sulfamide (or sulfoxamide, when selected), and in such a reaction two moles of hydrogen halide HX are liberated. In the above two reactions, the identities of the various substituents are as previously described, namely L is a divalent radical that may be either of

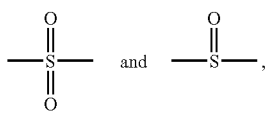

and $R_1$ may be any $C_1$ to $C_{20}$ hydrocarbyl group; and $R_2$ and $R_3$ are each independently selected from the group consisting of: hydrogen and any $C_1$ to $C_{20}$ hydrocarbyl group.

These reactions fall under the general reaction:

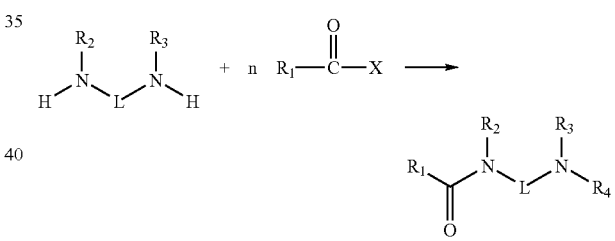

in which L is a divalent radical that may be either of

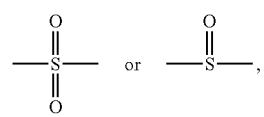

n preferably has the value of either one or two; $R_1$ may independently be any $C_1$ to $C_{20}$ hydrocarbyl group; $R_2$, and $R_3$ in the reactant may independently be hydrogen, or any $C_1$ to $C_{20}$ hydrocarbyl group, and $R_2$ and $R_3$ in the product are each independently hydrogen, any $C_1$ to $C_{20}$ hydrocarbyl group, or the group:

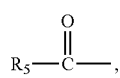

in which $R_5$ is independently hydrogen or any $C_1$ to $C_{20}$ hydrocarbyl group, and $R_4$ is hydrogen or the group:

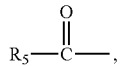

in which $R_5$ is independently hydrogen or any $C_1$ to $C_{20}$ hydrocarbyl group. Alternate preferred embodiments include the cases where n is selected to be 3 when at least one of $R_2$ and $R_3$ in the reactant are hydrogen, and where n is selected to be 4 when both of $R_2$ and $R_3$ in the reactant are hydrogen. The liberated HX is not specified in the general reaction but is recognized as being liberated by those skilled in the art, in a quantity that depends upon the total amount of acid halide and active hydrogen atoms present in the reactant sulfamide or sulfoxamide.

Thus, using a process as described above in combination with the specified starting materials, the invention provides compositions of matter useful for forming peroxygen acids, which comprise a nitrogenous compound having the structure:

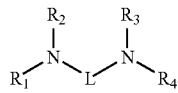

in which L is a divalent radical that is independently selected from the group consisting of:

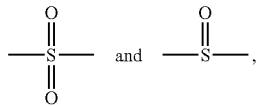

and wherein $R_1$, $R_2$, $R_3$, and $R_4$ are each independently selected from the group consisting of: hydrogen, any $C_1$ to $C_{20}$ hydrocarbyl group, and the group:

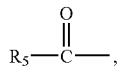

in which $R_5$ is in each occurrence independently hydrogen or any $C_1$ to $C_{20}$ hydrocarbyl group. In a preferred embodiment, at least one of $R_1$, $R_2$ $R_3$, and $R_4$ are the group:

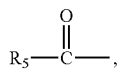

in which $R_5$ is in each occurrence independently hydrogen or any $C_1$ to $C_{20}$ hydrocarbyl group. In another preferred embodiment, at least one of $R_1$ and $R_2$ are the group:

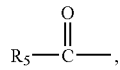

in which $R_5$ is in each occurrence independently hydrogen or any $C_1$ to $C_{20}$ hydrocarbyl group and at least one of $R_3$ and $R_4$ are the group:

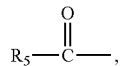

in which $R_5$ is in each occurrence independently hydrogen or any $C_1$ to $C_{20}$ hydrocarbyl group.

The processes in all of the these reactions set forth above are considered to be acylation reactions, and their reaction products are useful in preparing solutions containing peroxygen acids upon their being mixed with an aqueous peroxide such as hydrogen peroxide or a peroxide precursor, such as percarbonate or perborate anions, in aqueous media. The acylation reactions described above for preparing the precursors are preferably carried out in a solvent, which solvent is preferably an organic solvent in which the acid halide and sulfamide (or sulfoxamide, when employed) are mutually soluble. In addition, it is preferable to add a small amount of tertiary amine, such as a tri-alkyl amine such as triethylamine, trimethylamine, pyridine, etc. to the solution to facilitate the reaction between the acid halide and sulfamide (or sulfoxamide), as the use of tertiary amines for this purpose is known in the art.

It will be immediately recognized by those skilled in the art upon reading this specification that the identity of the hydrocarbyl groups $R_1$ and $R_5$ will often be the same, as in those cases when two moles of acid halide are combined with one mole of the sulfamide (or sulfoxamide when selected). However, it is possible for the identities of the hydrocarbyl groups $R_1$ and $R_5$ to be different from one another in a precursor product according to the invention, and such result is readily accomplished by first reacting a selected sulfamide (or sulfoxamide) having two active hydrogen atoms, either on the same nitrogen atom or on different nitrogen atoms, with a first acid halide, and then subsequently reacting the acylated product with a second acid halide having an R group that differs from that of the first acid halide. During the course of such reactions, owing to thermodynamic and kinetic equilibria, it is statistically probable that a portion of the reaction product will be one in which $R_2$ may comprise the group:

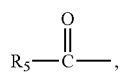

in which $R_5$ may comprise the same group as $R_1$, for the case when two moles of acid halide are reacted in a single reaction step with each sulfamide (or sulfoxamide) present, when the sulfamide (or sulfoxamide) initially comprises two active hydrogen atoms attached to the same nitrogen in the reactant (with $R_3$ and $R_4$ being as specified above) By the same token, in an alternate form of the invention $R_5$ in a radical:

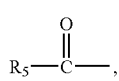

in the position of $R_2$ may comprise a different group than $R_1$, for the case when two moles of acid halide are reacted in two separate reaction steps with each sulfamide (or sulfoxamide) present, when the sulfamide (or sulfoxamide) initially comprises two active hydrogen atoms attached to the same nitrogen in the reactant. Thus, although the most kinetically favored reaction product is represented by:

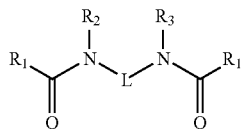

there will nevertheless also be present certain quantities of material represented by the structure:

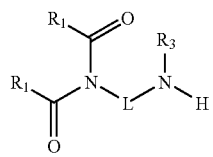

the relative amount of which depends on the nature of the $R_1$ group, as is readily appreciated by those skilled in the art, when the $R_2$ group in the reactant which results from the monoacylation of the sulfamide (or sulfoxamide) raw material:

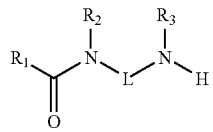

comprises hydrogen. Thus, the present invention also includes compositions having the general structure:

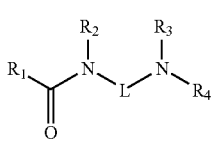

in which $R_2$ comprises the radical:

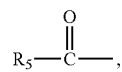

in which $R_5$ is independently hydrogen or any $C_1$ to $C_{20}$ hydrocarbyl group. However, the preferred inventive compounds are those described by the formula:

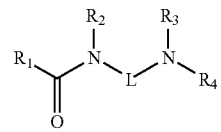

in which L is a divalent radical that is independently selected from the group consisting of:

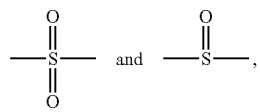

and wherein $R_1$ is independently any $C_1$ to $C_{20}$ hydrocarbyl group; $R_2$ and $R_3$ are each independently selected from the group consisting of: hydrogen and any $C_1$ to $C_{20}$ hydrocarbyl group; and $R_4$ is independently selected from the group consisting of: hydrogen, and the group

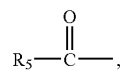

in which $R_5$ is independently hydrogen or any $C_1$ to $C_{20}$ hydrocarbyl group are water soluble at room temperature, are more efficient in generating peracids than currently-available commercial precursors, and these materials can be advantageously used as solid precursors to peroxy acids when mixed with hydrogen peroxide or a hydrogen peroxide precursor such as percarbonate or perborate.

The following preparatory methods are intended to be exemplary of the present invention and shall not be construed to be delimitive thereof in any respect.

EXAMPLE 1

Synthesis of diproprionyl sulfamide—To 100 ml of toluene in a flask equipped with a reflux condenser and a mechanical stirrer under moderate agitation are added 9.6 grams of sulfamide and 10.1 grams of triethylamine, and stirring is continued until complete dissolution occurs. Next, 9.25 grams of proprionyl chloride is added dropwise with stirring over the course of about 15 minutes, while the temperature of the flask is maintained below 60° C. After the addition of the proprionyl chloride is complete, the mixture is allowed to cool to room temperature, after which time it is filtered to remove the triethylamine hydrochloride by-product, which is discarded. The toluene is removed using a rotary evaporator until crystals just begin to form, at which time the flask contents are cooled to between about 2-8° C. overnight to complete crystallization process. The product is filtered, dried under vacuum, and stored in a dessicator. The overall reaction is:

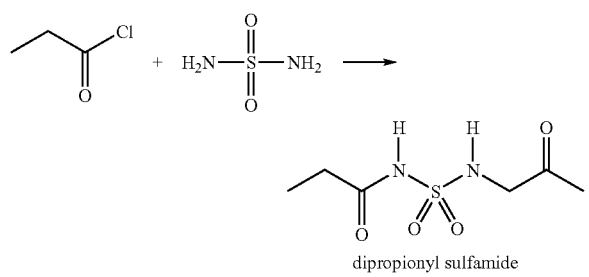

dipropionyl sulfamide

EXAMPLE 2

The procedure according to Example 1 is followed, except 13.0 grams of propionic anhydride is utilized in place of the proprionyl chloride.

EXAMPLE 3

Synthesis of dipropionyl sulfoxamide—To 100 ml of toluene in a round bottom flask equipped with a reflux condenser and a mechanical stirrer under moderate agitation are added 8.0 grams of sulfoxamide and 10.1 grams of triethylamine until dissolution is complete. Subsequently, 9.25 grams of proprionyl chloride is added dropwise with stirring by means of an addition funnel while taking care to maintain the mixture below 60° C. Following the addition the mixture is allowed to cool to room temperature, and is filtered to remove triethylamine hydrochloride by-product, which is discarded. The toluene is evaporated using a rotary evaporator until crystals just begin to form, after which time the contents of the flask are cooled to between 2-8° C. and allowed to stand overnight to complete crystallization process. The product is filtered, dried under a vacuum, and stored in a dessicator the overall reaction is:

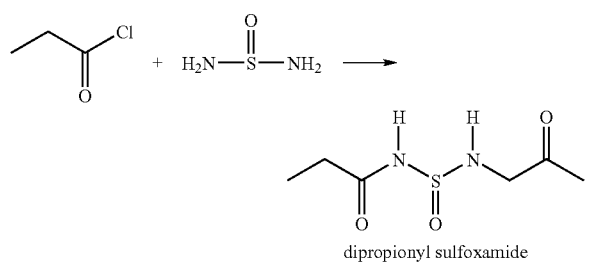

dipropionyl sulfoxamide

EXAMPLE 4

The procedure according to Example 3 is followed, except that 13.0 grams of propionic anhydride is utilized in place of the proprionyl chloride.

Practical Use Example

An equimolar amount of sodium perborate and dipropionyl sulfamide are mixed with water sufficient to generate ~0.4% perpropionic acid. To make one liter of product mix 4.8 grams of dipropionyl sulfamide with 4.65 grams of sodium perborate and add one liter of water. The reaction mixture will be initially basic, then as the reaction proceeds the pH will drop. Sufficient buffer such as sodium dihydrogen phosphate should be added such that the final pH is between ~6.5 and ~7.0. To enhance microbial activity, ionic or non-ionic surfactants such as dodecylbenzenesulfonic acid or Pluronic™ surfactants (BASF) may be added. Sequestering agents such as ethylenediaminetetraacetic (EDTA) acid may also be added.

For the sake of stability of an aqueous solution containing a nitrogenous compound according to embodiments of the invention, it is preferred that the aqueous solution contain a pH buffer. The buffer chosen is not critical as long as the pH is maintained preferably in the range of between about 5.0 to 7.0. A vast number of buffers are known to those skilled in the art, and any buffer known to those skilled in the art as being useful for maintaining an aqueous solution that contains a nitrogenous compound according to the invention in the range specified above may be used for this purpose, with the main proviso for suitability being that the components of such buffer are preferably stable with respect to the other chemical species in the aqueous solution and do not react therewith. Suitable buffer systems thus include without limitation: phosphate buffers; sulfate buffers; acetic/acetate buffers; propionic/proprionate buffers; $C_1$-$C_{10}$ mono- and polycarboxylic acid buffers; substituted carboxylic acids such as lactic, ascorbic, and tartaric acid buffers; and carboxylic acids that have unsaturation such as maleic and furmaric buffers. Buffer systems are known to contain salt pairs. Currently, the most preferred buffer is the dihydrogen phosphate buffer, adjusted to a pH of about 6.5.

Sequesterants may be used to advantage as a component of an aqueous solution that contains a nitrogenous compound according to the invention, for tying up or otherwise rendering chemically unavailable various species which may otherwise tend to interfere with the performance of the compounds and/or solutions of the invention. Suitable sequesterants include those commonly employed in the surfactant and other industries, including without limitation EDTA and its analogs, or analogous phosphonic acid salts, tartarates, citrates, and other species recognized by those skilled in the art as capable of functioning as a sequesterant.

Other soluble conventional materials may be present to advantage as a component of an aqueous solution that contains a nitrogenous compound according to embodiments of the invention, including corrosion inhibitors, dyes, perfumes, germicides, preservatives, e.g., QUATERNTUM™ 15 (Dow Chemical), anti-tarnishing agents, surfactants (for example anionic, cationic, nonionic, amphoteric or mixtures thereof), thickeners, chelating agents, antioxidants, and the like. Such other conventional materials may be used in the amounts they are normally used generally up to about 5% by weight, more preferably up to about 3% by weight.

Also provided by embodiments of the invention are processes for disinfecting a surface (including surfaces of implements such as surgical implements and other medical equipment or wares) which comprises the step of contacting a surface with an aqueous composition that is formed from mixing water, a source of peroxide, and a nitrogenous compound as described herein. Such a mixture contains a peroxy acid, whose identity is readily controllable by selecting the various molecular appendages, and such solutions have powerful disinfectant properties. Any source of peroxide, including those herein described are suitable, including hydrogen peroxide. In some embodiments, the source of peroxide is a solid compound, which upon being contacted with water yields a peroxide, including alkali metal salts and alkaline earth metal salts of percarbonates and perborates. Persulfates of these cations are suitable as are alkali metal and alkaline earth metal peroxides. In some embodiments, the aqueous composition which contains the peroxy acid generated according to the invention is formed using between about 0.1% and about 5% by weight of the nitrogenous compound, based on the total weight of the aqueous composition.

Also provided herein are processes for disinfecting various microbes, including bacteria, molds, fungi and their spores, from various articles and surfaces, which processes comprise generating an aqueous solution which contains a peroxy acid as described herein, and subsequently directing the vapor of the peroxy acid that is evolved from a solution so generated to a surface or article (including without limitation articles such as surgical implements and other medical equipment or wares) using conventional means of vaporization and direction, which may be selected from the group consisting of: heat, venturi nebulization, and sonication. Blowers and fans and other air or gas circulating equipment known to those skilled in the art may be beneficially employed. For purposes of this specification and claims, the word "surface" means any surface of any solid object, and includes without limitation walls, floors, ceilings, surgical instruments, medical wares, machinery, equipment, facilities, dwellings, garments, motorized vehicles, aircraft, windows, plumbing, corridors, etc.

Thus, in some embodiments, the mixing of the water, nitrogenous compound, and source of peroxide is conducted under conditions which enable evolution of vapors of peroxy acid so generated from the aqueous solution so formed by such mixing. Such conditions may be ambient conditions of standard temperature (298° K.) and pressure (1 atm), or may include elevated temperatures and reduced pressures. Typically, such vapors will contain some co-volatilized water. In some process embodiments involving the contacting of a surface or implement that is to be disinfected with an aqueous composition as taught herein, the contacting is accomplished by having the aqueous composition comprise a mixture of water vapor and the peroxy acid liberated by the solution formed from the mixing as provided herein. Stated another way, a surface or implement may be disinfected by contacting the subject surface or implement with a vapor that comprises a peroxy acid provided herein, with water being optionally present in such vapor in any amount between about 1% and 75% by partial pressure of such vapor.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. The present invention further includes all possible combinations of the features recited in the specification and/or any one of the various claims appended hereto with the features recited elsewhere in the specification and/or in any one or more of each of the remaining claims. For example, the present specification includes disclosure of a process according to claim 18 which comprises contacting a composition according to any of claims 1-17 with an aqueous peroxide. Accordingly, the presently disclosed invention is intended to cover all such modifications, alterations, and combinations.

What is claimed is:

1. A process for disinfecting a surface comprising the step of contacting said surface with an aqueous composition that is formed from mixing:
   a) water;
   b) a composition of matter which comprises a nitrogenous compound having the structure:

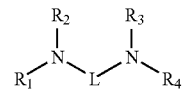

in which L is a divalent radical that is independently selected from the group consisting of:

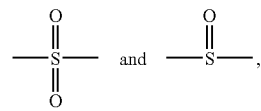

and wherein $R_1$, $R_2$, $R_3$, and $R_4$ are each independently selected from the group consisting of: hydrogen, any $C_1$ to $C_{20}$ hydrocarbyl group, and the group:

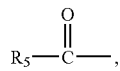

wherein both of the nitrogen atoms in said structure do not have the same substituents appended thereto; and
wherein both of the substituents in a pair selected from the group consisting of: $R_1$ and $R_2$; and $R_3$ and $R_4$ are the group:

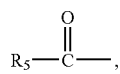

in which $R_5$ is independently in each occurrence hydrogen or any $C_1$ to $C_{20}$ hydrocarbyl group; and
wherein at least one of the groups of $R_1$, $R_2$, $R_3$, and $R_4$ which are not the group:

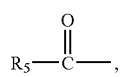

is hydrogen; and
   c) a source of peroxide.

2. A process according to claim 1 wherein said source of peroxide is a solid compound which upon being contacted with water yields a peroxide.

3. A process according to claim 1 wherein said source of peroxide is selected from the group consisting of: alkali metal salts of a percarbonate, alkaline earth metal salts of a percarbonate, alkali metal salts of a perborate, and alkaline earth metal salts of a perborate.

4. A process according to claim 1 wherein said source of peroxide is selected from the group consisting of: hydrogen peroxide and peroxide ions.

5. A process according to claim 1 wherein said aqueous composition is formed using between about 0.1% and about 5% by weight of said nitrogenous compound based on the total weight of said composition.

6. A process according to claim 1, wherein said mixing is conducted under conditions which enable evolution of vapors of peroxy acid from the aqueous solution formed.

7. A process according to claim 1, wherein said aqueous composition is in liquid or gaseous form.

8. A process for disinfecting a surface comprising the step of contacting said surface with an aqueous composition that is formed from mixing:
   a) water;
   b) a composition of matter which comprises a nitrogenous compound having the structure:

$$R_1\text{-}N(R_2)\text{-}L\text{-}N(R_3)\text{-}R_4$$

in which L is a divalent radical that is independently selected from the group consisting of:

$$-\underset{\underset{O}{\|}}{\overset{\overset{O}{\|}}{S}}- \quad \text{and} \quad -\overset{\overset{O}{\|}}{S}-,$$

and wherein $R_1$, $R_2$, $R_3$, and $R_4$ are each independently selected from the group consisting of: hydrogen, any $C_1$ to $C_{20}$ hydrocarbyl group, and the group:

$$R_5-\overset{\overset{O}{\|}}{C}-,$$

subject to the provisos that: both of the nitrogen atoms in said structure do not have the same substituents appended thereto; and wherein any three of $R_1$, $R_2$, $R_3$, and $R_4$ are the group:

$$R_5-\overset{\overset{O}{\|}}{C}-,$$

in which $R_5$ is independently in each occurrence hydrogen or any $C_1$ to $C_{20}$ hydrocarbyl group; and
   c) a source of peroxide.

9. A process according to claim 8 wherein the group of $R_1$, $R_2$, $R_3$, and $R_4$ which is not a group:

$$R_5-\overset{\overset{O}{\|}}{C}-,$$

is hydrogen.

10. A process according to claim 8 wherein the group of $R_1$, $R_2$, $R_3$, and $R_4$ which is not a group:

$$R_5-\overset{\overset{O}{\|}}{C}-,$$

is any $C_1$ to $C_{20}$ hydrocarbyl group.

11. A process according to claim 8 wherein said source of peroxide is a solid compound which upon being contacted with water yields a peroxide.

12. A process according to claim 8 wherein said source of peroxide is selected from the group consisting of: alkali metal salts of a percarbonate, alkaline earth metal salts of a percarbonate, alkali metal salts of a perborate, and alkaline earth metal salts of a perborate.

13. A process according to claim 8 wherein said source of peroxide is selected from the group consisting of: hydrogen peroxide and peroxide ions.

14. A process according to claim 8 wherein said aqueous composition is formed using between about 0.1% and about 5% by weight of said nitrogenous compound based on the total weight of said composition.

15. A process according to claim 8, wherein said mixing is conducted under conditions which enable evolution of vapors of peroxy acid from the aqueous solution formed.

16. A process according to claim 8, wherein said aqueous composition is in a liquid or gaseous form.

17. A process for disinfecting a surface comprising the step of contacting said surface with an aqueous composition that is formed from mixing:
   a) water;
   b) a composition of matter which comprises a nitrogenous compound having the structure:

$$R_1\text{-}N(R_2)\text{-}L\text{-}N(R_3)\text{-}R_4$$

in which L is a divalent radical that is independently selected from the group consisting of:

$$-\underset{\underset{O}{\|}}{\overset{\overset{O}{\|}}{S}}- \quad \text{and} \quad -\overset{\overset{O}{\|}}{S}-,$$

wherein all of $R_1$, $R_2$, $R_3$, and $R_4$ are the group:

$$R_5-\overset{\overset{O}{\|}}{C}-,$$

in which $R_5$ is independently in each occurrence hydrogen or any $C_1$ to $C_{20}$ hydrocarbyl group; and
   c) a source of peroxide.

18. A process according to claim 17 wherein said source of peroxide is a solid compound which upon being contacted with water yields a peroxide.

19. A process according to claim 17 wherein said source of peroxide is selected from the group consisting of: alkali metal salts of a percarbonate, alkaline earth metal salts of a percarbonate, alkali metal salts of a perborate, and alkaline earth metal salts of a perborate.

20. A process according to claim 17 wherein said source of peroxide is selected from the group consisting of: hydrogen peroxide and peroxide ions.

21. A process according to claim 17 wherein said aqueous composition is formed using between about 0.1% and about 5% by weight of said nitrogenous compound based on the total weight of said composition.

22. A process according to claim 17, wherein said mixing is conducted under conditions which enable evolution of vapors of peroxy acid from the aqueous solution formed.

23. A process according to claim 17, wherein said aqueous composition is in a liqiud or gaseous form.

24. A process for disinfecting a surface comprising the step of contacting said surface with an aqueous composition that is formed from mixing:
   a) water;
   b) a composition of matter which comprises a nitrogenous compound having the structure:

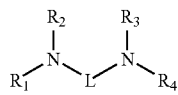

in which L is a divalent radical that is independently selected from the group consisting of:

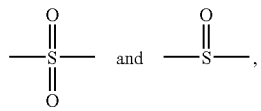

wherein $R_1$ and $R_4$ are represented by the group:

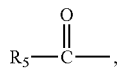

in which $R_5$ is independently in each occurrence hydrogen or any $C_1$ to $C_{20}$ hydrocarbyl group, and wherein $R_2$ and $R_3$ are each hydrogen; and
   c) a source of peroxcide.

25. A composition according to claim 24 wherein $R_5$ in each occurrence is independently selected from the group consisting of: hydrogen, a methyl, an ethyl, a propyl, and a butyl group.

26. A process according to claim 24 wherein said source of peroxide is a solid compound which upon being contacted with water yields a peroxide.

27. A process according to claim 24 wherein said source of peroxide is selected from the group consisting of: alkali metal salts of a percarbonate, alkaline earth metal salts of a percarbonate, alkali metal salts of a perborate, and alkaline earth metal salts of a perborate.

28. A process according to claim 24 wherein said source of peroxide is selected from the group consisting of: hydrogen peroxide and peroxide ions.

29. A process according to claim 24 wherein said aqueous composition is formed using between about 0.1% and about 5% by weight of said nitrogenous compound based on the total weight of said composition.

30. A process according to claim 24, wherein said mixing is conducted under conditions which enable evolution of vapors of peroxy acid from the aqueous solution formed.

31. A process according to claim 24, wherein said aqueous composition is in a liquid or gaseous from.

* * * * *